US005849685A

United States Patent [19]

Palmer

[11] Patent Number: 5,849,685

[45] Date of Patent: Dec. 15, 1998

[54] FRAGRANCE MATERIAL

[75] Inventor: Kenneth John Palmer, Ashford, United Kingdom

[73] Assignee: Quest International B.V., Naarden, Netherlands

[21] Appl. No.: 913,728

[22] PCT Filed: Mar. 4, 1996

[86] PCT No.: PCT/EP96/00931

§ 371 Date: Sep. 17, 1997

§ 102(e) Date: Sep. 17, 1997

[87] PCT Pub. No.: WO96/30469

PCT Pub. Date: Oct. 3, 1996

[30] Foreign Application Priority Data

Mar. 25, 1995 [EP] European Pat. Off. .............. 95104443

[51] Int. Cl.[6] .............................................. A61K 7/46

[52] U.S. Cl. .............................................. 512/9

[58] Field of Search .............................................. 512/9

[56] References Cited

U.S. PATENT DOCUMENTS

| | | | |
|---|---|---|---|
| 3,423,430 | 1/1969 | Cahn et al. | 512/9 |
| 4,606,849 | 8/1986 | Ansari et al. | 512/9 |
| 5,703,250 | 12/1997 | Bajgrowicz | 512/9 |

FOREIGN PATENT DOCUMENTS

| | | | |
|---|---|---|---|
| 0028780 | 5/1981 | European Pat. Off. | 512/9 |
| 2368271 | 10/1977 | France | 512/9 |
| 2533048 | 2/1977 | Germany | 512/9 |
| 2604553 | 8/1977 | Germany | 512/9 |

*Primary Examiner*—James H. Reamer
*Attorney, Agent, or Firm*—Pillsbury Madison & Sutro LLP

[57] ABSTRACT

The cyclic acetals of the 1,5-dioxaspiro[4,5]decane type which are substituted in the dioxane ring with 1–4 alkyl groups have organoleptic properties which make them useful as a fragrance materials. The alkyl groups each have 1–4 carbon atoms with the total number of carbon atoms in all alkyl groups together not exceeding 7. Preferably the cyclic acetals should have at least one alkyl group in the 4 position. A particularly preferred cyclic acetal is 3,3-dimethyl-4-isopropyl-1,5-dioxaspiro[4,5]decane.

15 Claims, 1 Drawing Sheet

Figure 1:
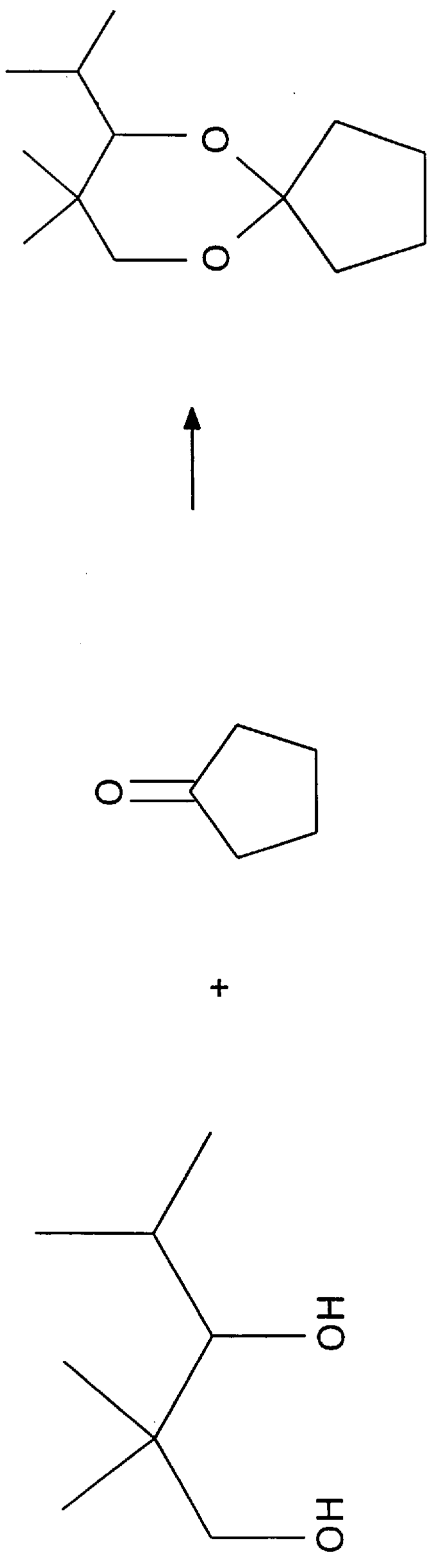

2,2,4-trimethyl-pentane-1,3-diol cyclopentanone 3,3-dimethyl-4-isopropyl-1,5-dioxaspiro[4,5]decane

FRAGRANCE MATERIAL

This application is the national phase of international application PCT/EP 96/00931, filed Mar. 4, 1996 which designated the U.S.

FIELD OF INVENTION

This invention concerns the use of cyclic acetals derived from cyclopentanone as a fragrance material.

BACKGROUND TO THE INVENTION

German Patent specification DT 2533048 discloses, inter alia, use of the cyclic acetal 3,3-dimethyl-4-isopropyl-1,5-dioxaspiro[4,5]decane as an antiburning, sun protection, sunburn treatment agent for use in cosmetics.

OUTLINE OF THE INVENTION

Cyclic acetals of the 1,5-dioxaspiro[4,5]decane type which are substituted in the dioxane ring with 1–4 alkyl groups have now been found to have organoleptic properties which make them useful as a fragrance materials. The alkyl groups should each have 1–4 carbon atoms with the total number of carbon atoms in all alkyl groups together not exceeding 7. Preferably the cyclic acetals should have at least one alkyl group in the 4 position, more preferably also at least one in the 3 position. Even more preferred are the acetals which have two methyl groups in the 3 position and one alkyl group in the 4 position. A particularly preferred cyclic acetal is 3,3-dimethyl-4-isopropyl-1,5-dioxaspiro[4,5]decane.

Therefore, in one aspect the invention provides fragrance compositions containing an olfactively effective amount of a cyclic acetal as described above, and particularly 3,3-dimethyl-4-isopropyl-1,5-dioxaspiro[4,5]decane.

In another aspect the invention provides use of a cyclic acetal as described above, and particularly 3,3-dimethyl-4-isopropyl-1,5-dioxaspiro[4,5]decane, for imparting fragrance properties to fragranced products.

The invention also provides use of a cyclic acetal as described above, and particularly 3,3-dimethyl-4-isopropyl-1,5-dioxaspiro[4,5]decane, for the manufacture of a fragrance composition.

A fragrance composition means a composition comprising various fragrance materials, and optionally a solvent, formulated to have certain useful fragrance characteristics. In most cases fragrance compositions are formulated to have a fragrance generally considered at least inoffensive and preferably pleasing to intended users of the composition. Fragrance compositions are used for imparting a desired odour to the skin and/or any product for which an agreeable odour is indispensable or desirable. Examples of such products are personal and household products including fabric washing powders, washing liquids, fabric softeners and other fabric care products; detergents and household cleaning, scouring and disinfection products; air fresheners, room sprays and pomanders; fine fragrances; soaps, bath and shower gels, shampoos, hair conditioners and other personal cleansing products; cosmetics such as creams, ointments, toilet waters, preshave, aftershave, skin—and other lotions, talcum powders, body deodorants and antiperspirants etc. Fragrance compositions are also used in products that would normally have an unattractive or offensive odour to mask this odour and produce an odour that is less unattractive or offensive. Products in this category include fuel odorants. The (pleasing) fragrance characteristics may be the main function of the product in which the fragrance compositions has been incorporated, as in the case of a fine fragrance, or may be ancillary to the main function of the product, as e.g. in the case of detergents, cleaning products and skin care products.

The acetals of the invention have attractive fragrance characteristics. The odour type is fruity, woody and floral. For the acetal 3,3-dimethyl-4-isopropyl-1,5-dioxaspiro[4,5]decane minty, sweet, damascone, leather, apple, camphor, pine and honey odour notes are also present.

The fragrance characteristics of the cyclic acetals of the invention mean that they find potential application as fragrance materials in a wide range of fragrance compositions and fragranced products, including those noted above.

Other fragrance materials which can be advantageously combined with the cyclic acetals according to the invention in a fragrance composition are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with the cyclic acetals according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)propanal, 3-(p-tert-butylphenyl)-propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane , 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphyl-cyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks tetralin musks isochroman musks macrocyclic ketones, macrolactone musks, ethylene brassylate.

Solvents which can be used for fragrance compositions which contain the cyclic acetals according to the invention are, for example: ethanol, isopropanol, diethyleneglycol monoethyl ether, dipropylene glycol, diethyl phthalate, triethyl citrate, isopropyl myristate, etc.

The quantities in which the cyclic acetals according to the invention can be used in fragrance compositions or in fragranced products may vary within wide limits and depend, inter alia, on the nature of the product, on the nature and the quantity of the other components of the fragrance composition in which a cyclic acetal is used and on the olfactive effect desired. It is therefore only possible to specify wide limits, which, however, provide sufficient information for the specialist in the art to be able to use the cyclic acetals according to the invention for his specific purpose. In fragrance compositions an amount of 0.1% by weight or more of the cyclic acetals according to the invention will generally have a perceptible olfactive effect. Preferably the amount is at least 1% by weight. The amount of the cyclic acetals according to the invention present in fragranced products will generally be at least 100 ppm by weight, preferably at least 1000 ppm.

The cyclic acetals may be used in fragrance compositions in an amount of up to about 50% by weight.

The acetals of the invention may occurs in two enantiomeric forms, depending on the number, the position and the structure of the substituent(s) and the invention covers both forms and also mixtures thereof.

The acetals of the invention are conveniently prepared by acid catalysed reaction of cyclopentanone with a suitable 1,3-diol, preferably a 3 substituted diol, more preferably a 2,3 substituted diol, even more preferably a 2,2-dimethyl-3-alkyl substituted diol, particularly 2,2,4-trimethylpentane-1,3-diol.

The invention will be further described, by way of illustration, in the following Examples and with reference to the accompanying drawings in which FIG. 1 shows as an example the reaction scheme for the preparation of 3,3-dimethyl-4-isopropyl-1,5-dioxaspiro[4,5]decane.

EXAMPLE 1

3,3-Dimethyl-4-isopropyl-1,5-dioxaspiro[4,5]decane was prepared on a laboratory scale in greater than 95% yield by the acid catalysed reaction of 2,2,4-trimethylpentane-1,3-diol with cyclopentanone using cyclohexane as solvent, with removal of the water produced via a Dean and Stark apparatus. The product was purified by distillation under vacuum using a short vigreux column. The reaction scheme is shown in FIG. 1.

The reaction was carried out in a 1 liter 3-necked flask equipped with a mechanical stirrer, a Dean and Stark apparatus fitted with a condenser, and a thermometer.

To the reaction flask was charged 2,2,4-trimethylpentane-1,3-diol (146 g, 1.0 mol), cyclopentanone (84 g, 1.0 mol), cyclohexane (250 g) and p-toluene sulphonic acid (0.25 g). The reaction mix was then heated to reflux and the water evolved collected into the Dean and Stark apparatus. When no more water was evolved, (theoretical=18 ml, 1.0 mol), the heating was terminated and the reaction allowed to cool to ambient temperature. At this stage, sodium bicarbonate solution (50 ml. 5% aqueous) was added to the flask and the contents stirred for 5 minutes. The reaction product was then poured into a separating flask and allowed to separate. The lower, aqueous phase was removed and discarded. The upper, organic phase was dried using anhydrous magnesium sulphate (2 g), then filtered and the solvent removed under vacuum using a rotary evaporator.

The crude product (218 g) was distilled using a short vigreux column. After a very small pre fraction the required product was collected at b.pt. 70° C. at 0.3 mb. The yield, 205 g, represented 96.7% of theoretical.

EXAMPLE 2

An apple fragrance for use in hair care products was prepared according to the following recipe.

| | % w/w |
|---|---|
| Hexyl salicylate | 15.0 |
| Traseolide (Q) | 30.0 |
| Hexyl-cinnamic aldehyde | 15.0 |

-continued

| | % w/w |
|---|---|
| Ligustral (Q) | 0.2 |
| Ligantraal (Q) | 0.3 |
| Pivacyclene (Q) | 7.5 |
| Gardocyclene (Q) | 5.0 |
| Allyl amyl-glycolate | 1.0 |
| Manzanate (Q) | 2.5 |
| cis-Hex-3-enyl salicylate | 1.0 |
| Ethyl methyl-phenyl-glycidate | 5.0 |
| Product of Example 1 | 10.0 |
| Diethyl phthalate | 7.5 |
| | 100 |

(Q) > Fragrance materials marketed by Quest International, Ashford, Kent, United Kingdom.

I claim:

1. Fragrance composition comprising known fragrance materials and in addition comprising an olfactively effective amount of a 1,5-dioxaspiro[4,5]decane which is substituted in the dioxane ring with 1–4 alkyl groups which each have 1–4 carbon atoms with the total number of carbon atoms in all alkyl groups together not exceeding 7.

2. Fragrance composition according to claim 1 comprising at least 0.1% by weight of the 1,5-dioxaspiro[4,5]decane.

3. Fragrance composition according to claim 2 comprising at least 1% by weight of the 1,5-dioxaspiro[4,5]decane.

4. Fragrance composition according to any one of claim 1 wherein the 1,5-dioxaspiro[4,5]decane has at least one alkyl group in the 4 position.

5. Fragrance composition according to claim 4 wherein the 1,5-dioxaspiro[4,5]decane also has at least one alkyl group in the 3 position.

6. Fragrance composition according to claim 5 wherein the 1,5-dioxaspiro[4,5]decane has two methyl groups in the 3 position and one alkyl group in the 4 position.

7. Fragrance composition according to claim 6 wherein the 1,5-dioxaspiro[4,5]decane is 3,3-dimethyl-4-isopropyl-1,5-dioxaspiro[4,5]decane.

8. Fragranced product comprising known fragrance materials and, in addition thereto, an olfactively effective amount of a 1,5-dioxaspiro[4,5]decane which is substituted in the dioxane ring with 1–4 alkyl groups which each have 1–4 carbon atoms with the total number of carbon atoms in all alkyl groups together not exceeding 7.

9. Fragranced product according to claim 8 comprising at least 100 ppm of the 1,5-dioxaspiro[4,5]decane.

10. Fragranced product according to claim 9 comprising at least 1000 ppm of the 1,5-dioxaspiro[4,5]decane.

11. Fragranced product according to any one of claim 8 wherein the 1,5-dioxaspiro[4,5]decane has at least one alkyl group in the 4 position.

12. Fragranced product according to claim 11 wherein the 1,5-dioxaspiro[4,5]decane also has at least one alkyl group in the 3 position.

13. Fragranced product according to claim 12 wherein the 1,5-dioxaspiro[4,5]decane has two methyl groups in the 3 position and one alkyl group in the 4 position.

14. Fragranced product according to claim 13 wherein the 1,5-dioxaspiro[4,5]decane is 3,3-dimethyl-4-isopropyl-1,5-dioxaspiro[4,5]decane.

15. A process for preparing a fragrance composition comprising known fragrance materials which comprises the step of adding thereto an olfactively effective amount of a 1,5-dioxaspiro[4,5]decane which is substituted in the dioxane ring with 1–4 alkyl groups which each have 1–4 carbon atoms with the total number of carbon atoms in all alkyl groups together not exceeding 7.

* * * * *